(12) United States Patent
Samain et al.

(10) Patent No.: US 10,731,193 B2
(45) Date of Patent: Aug. 4, 2020

(54) OLIGOSACCHARIDE PRODUCTION

(71) Applicant: GLYCOM A/S, Høsholm (DK)

(72) Inventors: Eric Samain, Gieres (FR); Pauline Peltier-Pain, Orleans (FR); Katrine Bych, Valby (DK); Ted Johanson, Virum (DK); Elise Champion, Toulouse (FR); Gyula Dekany, Sinnamon Park (AU)

(73) Assignee: GLYCOM A/S, Hørsholm (DK)

( * ) Notice: Subject to any disclaimer, the term of this patent is extended or adjusted under 35 U.S.C. 154(b) by 0 days.

(21) Appl. No.: 15/321,996

(22) PCT Filed: Jun. 29, 2015

(86) PCT No.: PCT/DK2015/050191
§ 371 (c)(1),
(2) Date: Dec. 23, 2016

(87) PCT Pub. No.: WO2015/197082
PCT Pub. Date: Dec. 30, 2015

(65) Prior Publication Data
US 2017/0175154 A1 Jun. 22, 2017

(30) Foreign Application Priority Data
Jun. 27, 2014 (DK) .................................. 2014 70392

(51) Int. Cl.
| C12P 19/18 | (2006.01) |
|---|---|
| C07K 14/245 | (2006.01) |
| C12N 15/52 | (2006.01) |
| C12N 9/10 | (2006.01) |
| C12N 9/12 | (2006.01) |
| C12N 9/24 | (2006.01) |
| C12N 9/38 | (2006.01) |

(52) U.S. Cl.
CPC ............ *C12P 19/18* (2013.01); *C07K 14/245* (2013.01); *C12N 9/1029* (2013.01); *C12N 9/1051* (2013.01); *C12N 9/1205* (2013.01); *C12N 9/2402* (2013.01); *C12N 9/2471* (2013.01); *C12N 15/52* (2013.01); *C12Y 203/01018* (2013.01); *C12Y 204/01149* (2013.01); *C12Y 302/01023* (2013.01); *C12Y 302/01026* (2013.01)

(58) Field of Classification Search
None
See application file for complete search history.

(56) References Cited

U.S. PATENT DOCUMENTS

| 2008/0145899 A1* | 6/2008 | Johnson ................. C12P 13/02 435/97 |
| 2009/0082307 A1 | 3/2009 | Samain et al. |
| 2012/0208181 A1* | 8/2012 | Merighi ................. C12N 9/00 435/6.1 |
| 2016/0024543 A1* | 1/2016 | Merighi ................. C07H 1/00 536/55.2 |

FOREIGN PATENT DOCUMENTS

| AU | 200062961 | 4/2001 |
| EP | 1149911 | 10/2001 |
| EP | 2239336 | 10/2010 |
| EP | 2371952 | 10/2011 |
| EP | 2405005 | 1/2012 |
| EP | 2405006 | 1/2012 |
| GB | 2155935 | 10/1985 |
| WO | 2007101862 | 9/2007 |
| WO | 2010051849 | 5/2010 |
| WO | 2010070104 | 6/2010 |
| WO | 2012007481 | 1/2012 |
| WO | 2012078311 | 6/2012 |
| WO | 2012112777 | 8/2012 |
| WO | 2013087884 | 6/2013 |
| WO | 2013182206 | 12/2013 |
| WO | 2014048439 | 4/2014 |
| WO | 2014067696 | 5/2014 |

OTHER PUBLICATIONS

K. Schmid et al. "Plasmid-Mediated Sucrose Metabolism in *Escherichia coli* K12: Mapping of the scr Gene of pUR400", Molecular Microbiology 2(1):1-8 (Year: 1988).*
Ruffing, A. et al., "Metabolic engineering of microbes for oligosaccharide and polysaccharide synthesis", Microbial Cell Factories, 2006, vol. 5(25).

(Continued)

*Primary Examiner* — Rebecca E Prouty
(74) *Attorney, Agent, or Firm* — Neal, Gerber & Eisenberg LLP

(57) ABSTRACT

The invention relates to a genetically modified microorganism for making a recombinant oligosaccharide, preferably of 3-8 monosaccharide units, more preferably of 3-5 monosaccharide units, particularly a HMO, which comprises one or more genes encoding a sucrose utilization system, so the microorganism can use sucrose as a carbon and energy source. The one or more genes encoding a sucrose utilization system are preferably one or more genes encoding a heterologous PTS-dependent sucrose utilization transport system, such as the scr genes.

8 Claims, 1 Drawing Sheet

(56) References Cited

OTHER PUBLICATIONS

De Bruyn, F. et al., "Development of an in vivo glucosylation platform by coupling production to growth: Production of phenolic glucosides by a glycosyltransferase of Vitis vinifera", Biotechnology and Bioengineering, 2015, vol. 112, pp. 1594-1603.
Priem, B. et al., "A new fermentation process allows large-scale production of human milk oligosaccharides by metabolically engineered bacteria", Glycobiology, 2002, vol. 12(4), pp. 235-240.
Ruffing, A. et al., "Metabolic engineering of Agrobacterium sp. for UDP-galactose regeneration and oligosaccharide synthesis", Metabolic Engineering, 2006, vol. 8, pp. 465-473.
Baumgartner, F. et al., "Construction of Escherichia coli strains with chromosomally integrated expression cassettes for the synthesis of 20-fucosyllactose," Microb. Cell Fact., 2013, vol. 12(40).
Bruschi, M. et al., "A transferable sucrose utilization approach for non-sucrose-utilizing Escherichia coli strains," Biotechnol. Adv., 2012, vol. 30, 1001-1010.
Drouillard, S. et al., "Large-scale synthesis of H-antigen oligosaccharides by expressing Helicobacter pylori alpha1,2-fucosyltransferase in metabolically engineered Escherichia coli cells," Angew. Chem. Int. Ed., 2006, vol. 45 (11), pp. 1778-1780.
Fort, S. et al., "Biosynthesis of Conjugatable Saccharidic Moieties of GM2 and GM3 Gangliosides by Engineered E. coli," Chem. Comm., 2005, vol. 20, pp. 2558-2560.
Khamduang, M. et al., "Production of L-phenylalanine from glycerol by a recombinant Escherichia coli," J. Ind. Microbiol. Biotechnol., 2009, vol. 36, pp. 1267-1274.
Kim, J. R. et al., "Construction of homologous and heterologous synthetic sucrose utilizing modules and their application for carotenoid production in recombinant Escherichia coli," Biores. Technol., 2013, vol. 130, pp. 288-295.
Lee, W. et al., "Whole cell biosynthesis of a functional oligosaccharide, 2'-fucosyllactose, using engineered Escherichia coli," Microb. Cell Fact., 2012, vol. 11(48).
Sabri, S. et al., "Molecular Control of Sucrose Utilization in Escherichia coli W, an Efficient Sucrose-Utilizing Strain," Appl. Environ. Microbiol, 2013, vol. 79(2), pp. 478-487.
Reid, S. J. et al., "Sucrose utilisation in bacteria: genetic organisation and regulation," Appl. Microbiol. Biotechnol., 2005, vol. 67, pp. 312-321.
Olson, M. M. et al., "Production of tyrosine from sucrose or glucose achieved by rapid genetic changes to phenylalanine-producing Escherichia coli strains," Appl. Microbiol. Biotechnol., 2007, vol. 74, pp. 1031-1040.
Gabor, E. et al., "The phosphoenolpyruvate-dependent glucose-phosphotransferase system from Escherichia coli K-12 as the center of a network regulating carbohydrate flux in the cell," European Journal of Cell Biology, 2011, Col. 90, pp. 711-720.
Jahreis, K. et al., "Adaptation of Sucrose Metabolism in the Escherichia coli Wild-Type Strain EC3132," Journal of Bacteriology, 2002, vol. 184(19), pp. 5307-5316.
Wang, J. et al., "Modeling of inducer exclusion and catabolite repression based on a PTS-dependent sucrose and non-PTS-dependent glycerol transport systems in Escherichia coli K-12 and its experimental verification," Journal of Biotechnology, 2001, vol. 92, pp. 133-158.
Gosset, G., "Improvement of Escherichia coli production strains by modification of the phosphoenolpyruvate:sugar phosphotransferase system," Microbial Cell Factories, 2005, vol. 4(14).
Postma, P. W. et al., "Phosphoenolpyruvate:Carbohydrate Phosphotransferase Systems of Bacteria," Microbiological Reviews, 1993, vol. 57(3), pp. 543-594.
Titgemeyer, F. et al., "Molecular analysis of the scrA and scrB genes from Klebsiella pneumoniae and plasmid pUR400, which encode the sucrose transport protein Enzyme IIscr of the phosphotransferase system and a sucrose-6-phosphate invertase," Mol. Gen. Genet., 1996, vol. 250, pp. 197-206.
Mohamed, E. T., et al., "Generation of an E. coli platform strain for improved sucrose utilization using adaptive laboratory evolution," Microbial Cell Factories, 2019, vol. 18, pp. 1-14.
PLOS Collections. (Oct. 26, 2017). Negative Results: A Crucial Piece of the Scientific Puzzle [Blog post]. Retrieved from https://blogs.plos.org/everyone/2017/10/26/negative-results-a-crucial-piece-of-the-scientific-puzzle/.

* cited by examiner

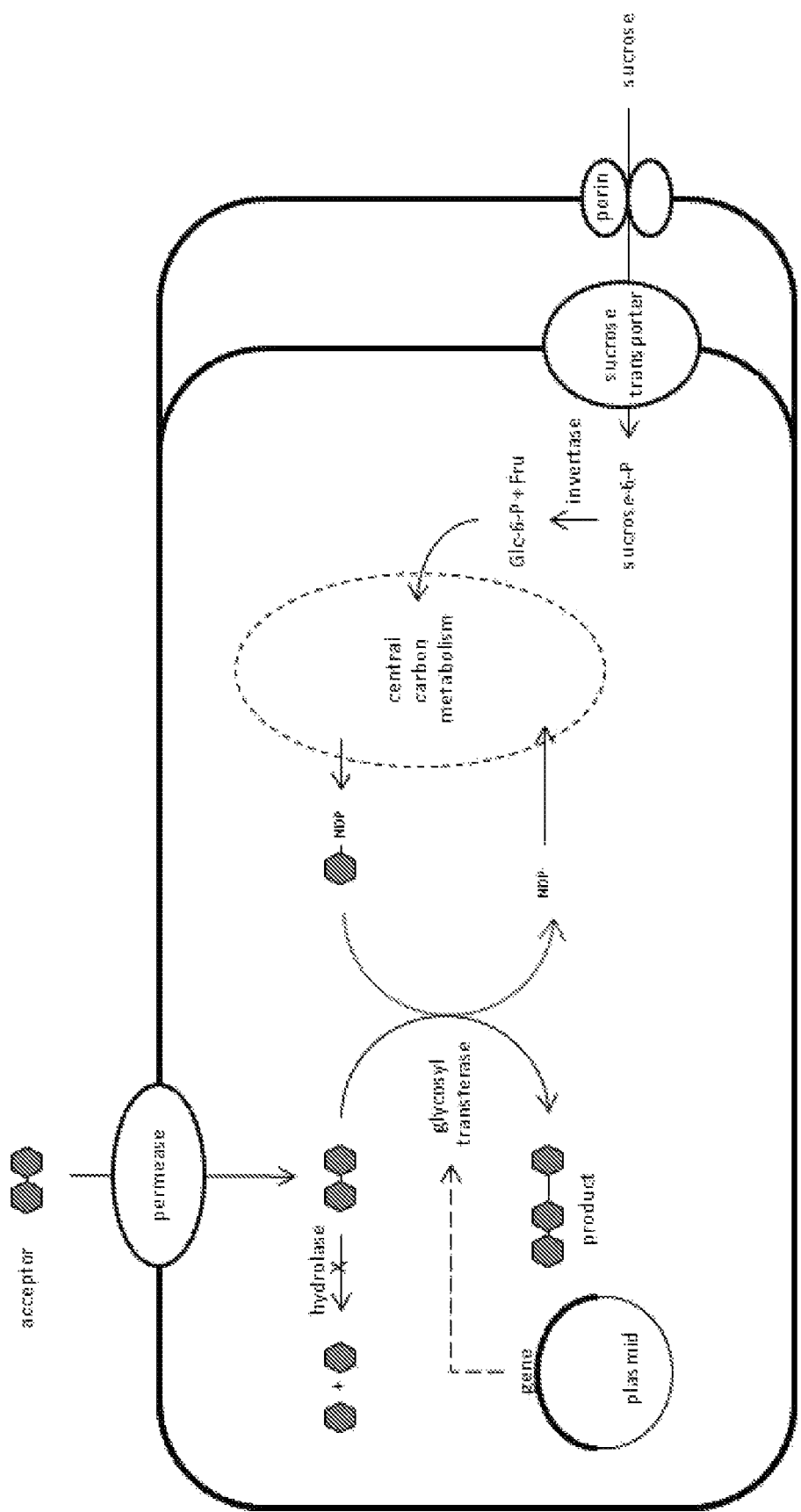

US 10,731,193 B2

OLIGOSACCHARIDE PRODUCTION

FIELD OF THE INVENTION

The present invention relates to the field of biotechnology, notably to a microbial production of recombinant oligosaccharides, particularly of human milk oligosaccharides (HMOs), using a genetically modified microorganism, particularly E. coli, using sucrose as its exclusive carbon source.

BACKGROUND OF THE INVENTION

The fermentative syntheses of foreign or exogenous oligosaccharides using recombinant microorganisms have recently become of great commercial and industrial interest. In such syntheses, oligosaccharides of interest would be synthesized by enzymatic glycosylation of sugar acceptors mediated by one or more heterologous glycosyl transferases of the microorganisms, and the one or more activated sugar nucleotides necessary for glycosylation would be produced by the same microorganism through overexpressing one or more genes encoding endogenous activated sugar nucleotide producing enzymes. The metabolic pathways of such syntheses require a carbon source which is mainly a simple carbon building block, typically glycerol or glucose (see e.g. WO 01/04341, Priem et al. *Glycobiology* 12, 235 (2002), Fort et al. *Chem. Comm.* 2558 (2005), Drouillard et al. *Angew. Chem. Int. Ed.* 45, 1778 (2006), WO 2010/070104, WO 2012/112777, WO 2013/182206, WO 2014/048439). In some syntheses, lactose can be the carbon source if it also serves as an acceptor (Lee et al. *Microb. Cell Fact.* 11:48 (2012)). As the microorganisms have been genetically manipulated, antibiotic-resistance selection marker genes have been utilized to separate the transformed microorganisms from the non-transformed ones in the inoculum and the fermentation broth. However, the use of antibiotics has been avoided by integrating the genes coding for enzymes involved in the de novo biosynthesis of the donor sugar in the chromosome of the microorganisms (Baumgartner et al. *Microb. Cell Fact.* 12:40 (2013)).

Around 50% of wild-type E. coli are able to utilize sucrose as a carbon and energy source, but most of them are pathogenic. The E. coli strains used mainly in industry to synthesize chemical materials cannot live and grow on sucrose (Bruschi et al. *Biotechnol. Adv.* 30, 1001 (2012)). However, in some cases, sucrose can be a cheaper carbon and energy source. For this reason, attempts have been made to create suck strains of E. coli that can live and grow on sucrose (e.g. Sabri et al. *Appl. Environ. Microbiol* 79, 478 (2013)) and produce industrially profitable products by them such as amino acids, biofuel, carotenoids etc. (e.g. EP-A-1149911, EP-A-2239336, EP-A-2371952, EP-A-2405006, WO 2010/051849, WO 2012/078311, Kim et al. *Biores. Technol.* 130, 288 (2013)). However, these suck transformants have generally been less productive than suc⁻ strains (Khamduang et al. *J. Ind. Microbiol. Biotechnol.* 36, 1267 (2009)).

WO 2012/007481 describes E. coli transformants that express either a sucrose phosphorylase or a sucrose invertase in combination with a fructokinase. Thereby, the microorganism is able to produce 2'-fucosyllactose, utilizing sucrose as its main carbon source. Furthermore, WO 2014/067696 describes an E. coli transformant comprising a csc-gene cluster that enables it to grow on sucrose and produces fucose.

There has been, however, a continuing need for alternative processes for making recombinant oligosaccharides, particularly HMOs, using transformed microorganisms that are able to utilize more effectively sucrose as a carbon and energy source.

SUMMARY OF THE INVENTION

A first aspect of the invention relates to a process for making a recombinant oligosaccharide, preferably of 3-8 monosaccharide units, more preferably of 3-5 monosaccharide units, particularly a HMO, by glycosylating a carbohydrate acceptor which is preferably lactose and which is not sucrose, comprising the steps of:

a) providing a cell, preferably an E. coli cell, that can internalize said acceptor into said cell and comprises
   a recombinant gene encoding a glycosyl transferase which is able to transfer a glycosyl residue of an activated sugar nucleotide to said acceptor, internalized in said cell, and
   a biosynthetic pathway to make said activated sugar nucleotide in said cell, b) culturing said cell in the presence of said acceptor and sucrose, and c) separating said oligosaccharide from said cell, from the culture medium or from both, said process being characterized in that said cell also comprises one or more genes encoding a sucrose utilization system, preferably encoding a heterologous sucrose utilization system, more preferably encoding a heterologous PTS-dependent sucrose utilization transport system, still more preferably scr genes, so that said cell can use sucrose as a carbon source, preferably the main carbon source, more preferably the sole carbon source, for making said activated sugar nucleotide and as an energy source, preferably the main energy source, more preferably the sole energy source, for making said oligosaccharide.

A second aspect of the invention relates to a cell, preferably an E. coli cell, that can internalize a carbohydrate acceptor, which is preferably lactose and which is not sucrose, into said cell and that comprises:

a recombinant gene encoding a glycosyl transferase which is able to transfer a glycosyl residue of an activated sugar nucleotide to said acceptor, internalized in said cell, a biosynthetic pathway to make said activated sugar nucleotide in said cell, and one or more genes encoding a sucrose utilization system, preferably a heterologous sucrose utilization system, more preferably scr genes, so that said cell can use sucrose as a carbon source, preferably the main carbon source, more preferably the sole carbon source.

BRIEF DESCRIPTION OF THE FIGURE

The FIGURE is intended to illustrate the invention further. It is not intended to limit the subject matter of the invention thereto.

The engineered microorganism is a fully metabolically active cell in which the growth and the oligosaccharide synthesis may proceed simultaneously. The cell comprises a heterologous PTS-dependent sucrose utilization transport system containing a sucrose specific porin (facilitates the sucrose diffusion through the outer membrane), a sucrose transport protein (provides intracellular sucrose-6-phosphate from extracellular sucrose) and a sucrose-6-phosphate hydrolase (provides glucose-6-phosphate and fructose). The oxidation of glucose-6-phosphate and fructose provides biological energy source by the organism's own metabolic system. Also, glucose-6-phosphate and fructose serve as carbon source for producing sugar nucleotides in the cell's natural biosynthetic pathway. The so-produced sugar nucleotides are donors for glycosylating carbohydrate acceptors (e.g. lactose), internalized through a specific permease by the cell, and thereby manufacturing oligosaccharides of interest. The glycosylation is mediated by one or more glycosyl transferases which are directly produced by expressing heterologous genes. The organism lacks any enzyme degrading either the acceptor or the oligosaccharide product in the cell.

DETAILED DESCRIPTION OF THE INVENTION

It has been surprisingly discovered that an exogenous mono- or disaccharide acceptor, preferably lactose, can be internalized in a suitable genetically transformed microorganism, particularly E. coli, by a transport mechanism involving permeases of the microorganism, that this carbohydrate acceptor can be glycosylated in the microorganism using sucrose as its carbon and energy source, and that an exogenous oligosaccharide can be produced and separated in good yield. Thereby, an efficient, cheap and easily up-scalable process for producing oligosaccharides can be obtained. In order to make the process successful, a special oligosaccharide-producing microorganism is needed that can live on sucrose, utilize sucrose for the metabolic syntheses of the necessary nucleotide sugar donors for glycosylaton, can internalize simple carbohydrate acceptors and perform glycosylation reactions on them for synthesizing more complex oligosaccharides.

The invention therefore, in a first aspect, involves a process of making an oligosaccharide by:
  a) providing a cell of a microorganism, preferably an E. coli cell, that can internalize sucrose and a carbohydrate acceptor, preferably lactose, into said cell and that comprises:
    a recombinant gene encoding a glycosyl transferase which can transfer a glycosyl residue of an activated sugar nucleotide to the acceptor within the cell, and
    a biosynthetic pathway for making the activated sugar nucleotide from sucrose,
  b) culturing the cell in an aqueous culture medium in the presence of the acceptor and sucrose, and
  c) separating the oligosaccharide product from the cell from the culture medium or from both.

The process features the cell being transformed with one or more foreign genes encoding a sucrose utilization system that allows the cell to use sucrose as a carbon source, preferably the main carbon source, more preferably the sole carbon source, for the biosynthesis of the activated sugar nucleotide by the cell. The sucrose utilization system, with which the cell is transformed, also preferably allows the cell to use sucrose as an energy source, preferably the main energy source, more preferably the sole energy source, for the biosynthesis of the oligosaccharide.

In accordance with this invention, the term "carbohydrate acceptor" or "acceptor" preferably means a mono- or disaccharide other than sucrose and its glycosides. A monosaccharide acceptor or a monosaccharide part of a disaccharide acceptor can comprise any 5-6 carbon atom sugar moiety that is an aldose (e.g. D-glucose, D-galactose, D-mannose, D-ribose, D-arabinose, L-arabinose, D-xylose, etc.), ketose (e.g. D-fructose, D-sorbose, D-tagatose, etc.), deoxysugar (e.g. L-rhamnose, L-fucose, etc.) or deoxy-aminosugar (e.g. N-acetylglucosamine, N-acetylmannosamine, N-acetylgalactosamine, etc.). In a glycoside-type carbohydrate acceptor the sugar moiety is attached to a non-sugar residue (aglycon) by either a covalent bond, which is a direct linkage between the glycosidic carbon atom of the sugar residue and any atom of the non-sugar moiety, or by a linker, which consists of one, two, three or four atoms such as —O—, —C—, —NH—, —N(OH)—, —S—, —C(=O)—, —C(=S)—, —C(=NH)—, —C(=N—OH)—, —C(=O)—O—, —O—C(=O)—, —C(=O)—S—, —S—C(=O)—, —C(=S)—O—, —O—C(=S)—, —C(=S)—S—, —S—C(=S)—, —C(=O)—NH—, —NH—C(=O)—, —C(=NH)—O—, —O—C(=NH)—, —C(=S)—NH—, —NH—C(=S)—, —C(=NH)—S— and —S—C(=NH). Thus, the C-1 (in case of aldoses) or C-2 (in the case of ketoses) anomeric carbon atom at the reducing end of the mono- or disaccharide residue is linked to the non-sugar moiety by a covalent bond or a linker forming a O-, N-, S- or C-glycoside. Preferably, the aglycon of these glycosidic derivatives, with or without a linker, is one of the following groups:

a) —$OR_A$, wherein $R_A$ is a linear or branched hydrocarbon chain having, when saturated, 1-24, preferably 1-6 carbon atoms (such as methyl, ethyl, n-propyl, i-propyl, n-butyl, i-butyl, s-butyl, t-butyl, n-hexyl, etc.) or, when unsaturated, 2-24, preferably 2-6 carbon atoms (such as vinyl, allyl, propargyl, etc.), or $R_A$ means an aryl moiety (a homoaromatic group such as phenyl or naphthyl), or $R_A$ means a group removable by hydrogenolysis, that is a group whose bond attached to the oxygen can be cleaved by addition of hydrogen in the presence of catalytic amounts of palladium, Raney nickel or another appropriate metal catalyst known for use in hydrogenolysis, resulting in the regeneration of an OH group; such protecting groups are well known to the skilled man and are discussed in *Protective Groups in Organic Synthesis*, PGM Wuts and TW Greene, John Wiley & Sons 2007. Suitable groups include benzyl, diphenylmethyl (benzhydryl), 1-naphthylmethyl, 2-naphthylmethyl or triphenylmethyl (trityl) groups. Any of the above mentioned $R_A$ groups can be optionally substituted by one or more groups selected from: alkyl (only for aryl and group removable by hydrogenolysis), hydroxy, alkoxy, carboxy, oxo, alkoxycarbonyl, alkylcarbonyl, formyl, aryl, aryloxy-carbonyl, aryloxy, arylamino, arylcarbonyl, amino, mono and dialkylamino, carbamoyl, mono- and dialkyl-amino-carbonyl, alkyl-carbonylamino, cyano, alkanoyloxy, nitro, alkylthio and halogen; in case of a group removable by hydrogenolysis, such substitution, if present, is preferably on the aromatic ring(s);

b) —X—$R_B$, wherein X is N or S, and $R_B$ means linear or branched hydrocarbon chain having, when saturated, 1-24, preferably 1-6 carbon atoms (such as methyl, ethyl, n-propyl, i-propyl, n-butyl, i-butyl, s-butyl, t-butyl, n-hexyl, etc.) or, when unsaturated, 2-24, preferably 2-6 carbon atoms (such as vinyl, allyl, propargyl, etc.), or $R_B$ means an aryl moiety (a homoaromatic group such as phenyl or naphthyl), or $R_B$ means a benzyl group. Any of the above mentioned $R_B$ groups can be optionally substituted by one or more groups selected from: alkyl (only for aryl and benzyl), hydroxy, alkoxy, carboxy, oxo, alkoxycarbonyl, alkylcarbonyl, formyl, aryl, aryloxy-carbonyl, aryloxy, arylamino, arylcarbonyl, amino, mono and dialkylamino, carbamoyl, mono- and dialkyl-amino-carbonyl, alkyl-carbonylamino, cyano, alkanoyloxy, nitro, alkylthio and halogen;

c) a group that links the anomeric carbon atom and the adjacent carbon atom to each other by a —NH—C(=O)—

O— bridge, thus forming a fused 5-membered ring as depicted below in case of an aldose:

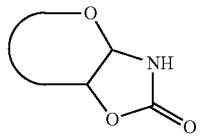

d) azide;
e) —NH—C(R")=C(R')$_2$, wherein each R' independently is an electron withdrawing group selected from —CN, —COOH, —COO-alkyl, —CO-alkyl, —CONH$_2$, —CONH-alkyl and —CON(alkyl)$_2$, or wherein the two R'-groups are linked together and form —CO—(CH$_2$)$_{2-4}$—CO— and thus form with the carbon atom, to which they are attached, a 5-7 membered cycloalkan-1,3-dione, in which dione any of the methylene groups is optionally substituted with 1 or 2 alkyl groups, and wherein R" is H or alkyl;
f) a residue of an amino acid, which can be any natural or non-natural amino acid, that is an alkanoic acid derivative having at least one amino group as a substituent. Preferably, the amino acid is selected from the group consisting of: α-amino acids and β-amino acids such as Ala, Arg, Asn, Asp, Cys, Glu, Gln, Gly, His, Ile, Leu, Lys, Met, Phe, Pro, Ser, Thr, Trp, Tyr, Val, hydroxyproline, α-methylserine, β-alanine, etc. These amino acids can be either directly or via a linker as defined above (e.g. for urea-linked glycopeptides see WO 2009/040363) bound to the carbohydrate at its C-1 (in case of aldoses) or C-2 (in the case of ketoses) anomeric carbon atom thus forming O-, N-, S- or C-glycosides. O-Glycosides (O-glycans) can be formed involving OH-containing amino acids such as serine, threonine, hydroxyproline, etc., N-glycosides (N-glycans) can be made using the α-, β-, etc. amino group of any amino acid or the additional amino group of the side chain of e.g. lysine, asparagine or glutamine, S-glycosides can be made using cystein, while C-glycosides (C-glycans) contain a C—C bond coupling a C-atom of the amino acid to the anomeric carbon atom of the non-reducing end of the oligosaccharide part;
g) a polyethylene glycol residue. Polyethylene glycol (PEG) is a water soluble polyether of molecular formula C$_{2n}$H$_{4n+2}$O$_{n+1}$, having oxyethylene (—CH$_2$—O—CH$_2$— or CH$_2$—CH$_2$—O—) repeating units and wherein n is 2 to 100, preferably 2 to 50, particularly 2 to 25, more particularly 2 to 10. Lower molecular weight PEGs are available in a purified form and are referred to as a "monodisperse PEG", and are also available as mixtures of PEGs and are referred to as a "polydisperse PEG". With regard to their geometry, PEGs can be in a linear, branched, star or comb configuration. Linear PEGs are preferably lower molecular weight PEGs (i.e., n is 2 to 10, preferably 3 to 6). Branched PEGs preferably have 3 to 10 linear, preferably lower molecular weight, PEG chains emanating from a central core group. Star PEGs preferably have 10 to 100 linear or branched, preferably lower molecular weight, PEG chains emanating from a central core group. Comb PEGs have multiple linear, branched and/or star, preferably lower molecular weight, PEG chains bonded to a polymer backbone. Terminal primary hydroxy group of PEGs can be bonded by an ether bond with an alkyl group, preferably methyl. In addition, their terminal hydroxy group can be replaced by amino, alkyl amino, dialkyl amino, acylamino, thiol or alkyl thio groups or their terminal hydroxymethyl group can be oxidized to a carboxyl, which can be esterified or be present in amide form with ammonia or a primary or secondary amine. The attachment is a glycosidic-like bond;
h) a polyvinyl alcohol residue. Polyvinyl alcohol (PVA) is a water-soluble polymer of molecular formula (C$_2$H$_4$O)$_x$ having —CH$_2$—CH(OH)— monomer units. When attached to carbohydrate, any of the OH-gropus can be glycosylated;
i) an α,β-unsaturated amido group of formula A

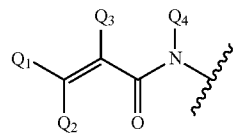

wherein Q$_1$, Q$_2$, Q$_3$ and Q$_4$ are, independently, H and C$_1$-C$_6$-alkyl, which alkyl optionally can be substituted with halogen, OH, nitro or phenyl groups. The residue of formula A, via its N atom, is linked to the sugar by a covalent bond, preferably to the anomeric carbon atom of the carbohydrate in the form of an N-glycoside; or
j) an α,β-unsaturated carbonyl group of formula B

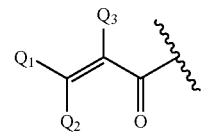

wherein Q$_1$, Q$_2$ and Q$_3$ are as defined at residue of formula A.

Preferably, the carbohydrate acceptor is a galactosyl disaccharide, particularly lactose.

Also in accordance with this invention, the term "oligosaccharide product" or "oligosaccharide" preferably means a glycosylated derivative of a carbohydrate acceptor disclosed above wherein a glycosyl residue is attached to the carbohydrate moiety of the carbohydrate acceptor by inter-glycosidic linkage. Preferably, an oligosaccharide product is of 3-8 monosaccharide units, particularly of 3-5 monosaccharide units. The oligosaccharide product of this invention is a recombinant product, i.e., it is made by a genetically transformed microorganism and is foreign or heterologous to the microorganism.

Further in accordance with this invention, the term "microorganism" or "cell" preferably means a cell of a microorganism, especially an *E. coli* cell, in which there is at least one alteration in its DNA sequence. The alteration can result in a change in the original characteristics of the wild type cell, e.g., the modified cell is able to perform additional chemical transformation due to the introduced new genetic material that encodes the expression of an enzymes not being in the wild type cell, or is not able to carry out transformation like degradation due to removal of gene/genes (knockout). A genetically modified cell can be produced in a conventional manner by genetic engineering techniques that are well-known to those skilled in the art.

The genetically modified microorganism or cell used in the process of this invention can be selected from the group consisting of bacteria and yeasts, preferably a bacterium. Bacteria are preferably selected from the group of: *Escherichia coli, Bacillus* spp. (e.g. *Bacillus subtilis*), *Campy-* lobacter pylori, Helicobacter pylori, Agrobacterium tumefaciens, Staphylococcus aureus, Thermophilus aquaticus, Azorhizobium caulinodans, Rhizobium leguminosarum, Neisseria gonorrhoeae, Neisseria meningitis, Lactobacillus spp., Lactococcus spp., Enterococcus spp., Bifidobacterium spp., Sporolactobacillus spp., Micromomospora spp., Micrococcus spp., Rhodococcus spp., Pseudomonas, among which E. coli is preferred.

The process of this invention also involves transporting the exogenous carbohydrate acceptor, preferably lactose, into the genetically modified microorganism for glycosylation to produce a foreign oligosaccharide of interest, preferably without adversely affecting the basic functions of the cell or destroying its integrity. In one embodiment, the transport takes place via a passive mechanism, during which the exogenous acceptor diffuses passively across the plasma membrane of the cell. Diffusion of the acceptor into the microorganism is a function of the concentration differences between the fermentation broth and the extra- and intracellular space of the cell with respect to the acceptor, whereby the acceptor passes from the place of higher concentration to the place of lower concentration. In another embodiment, the acceptor is internalized with the aid of an active transport. In such a case, the genetically modified microorganism contains transporter proteins, called permeases, which act as enzymes and with which the microorganism is able to admit exogenous substances and to concentrate them in the cytoplasm. Specifically, lactose permease (LacY) acts specifically on galactose, simple galactosyl disaccharides such as lactose and their glycosides. The specificity towards the sugar moiety of the exogenous carbohydrate acceptor to be internalized can be altered by mutation of the microorganism by means of conventional recombinant DNA manipulation techniques. In a preferred embodiment, the internalization of exogenous lactose or its derivative takes place via an active transport mechanism mediated by a lactose permease. The genetically modified microorganism preferably lacks any enzyme activity (such as LacZ) that would degrade the acceptor. Likewise, the microorganism is not able to hydrolyze or degrade the oligosaccharide product.

Moreover, the genetically modified cell used in the process of the invention comprises one or more endogenous or recombinant genes encoding one or more glycosyl transferase enzymes that are able to transfer the glycosyl residue of an activated sugar nucleotide to the internalized acceptor. The gene or an equivalent DNA sequence thereof, if it is recombinant, can be introduced into the cell by conventional techniques, e.g. using an expression vector or by chromosomal intergration. The origin of the heterologous nucleic acid sequence can be any animal (including human) or plant, eukaryotic cells such as those from *Saccharomyces cerevisae, Saccharomyces pombe, Candida albicans* or from algae, prokaryotic cells such as those originated from *E. coli, Bacteroides fragilis, Photobacterium sp., Bacillus subtilis, Campylobacter pylori, Helicobacter pylori, Agrobacterium tumefaciens, Staphylococcus aureus, Thermophilus aquaticus, Azorhizobium caulinodans, Rhizobium leguminosarum, Rhizobium meliloti, Neisseria gonorrhoeae* and *Neisseria meningitidis*, or virus. The glycosyl transferase enzyme/enzymes expressed by the protein(s) encoded by the gene(s) or equivalent DNA sequence(s) are preferably glucosyl transferases, galactosyl transferases, N-acetylglucosaminyl transferases, N-acetylgalactosaminyl transferases, glucuronosyl transferases, xylosyl transferases, mannosyl transferases, fucosyl transferases, sialyl transferases and the like. In a preferred embodiment, the glycosyl transferases are selected from the group consisting of β-1,3-N-acetylglucosaminyl-transferase, β-1,6-N-acetylglucosaminyl-transferase, β-1,3-galactosyl-transferase, β-1,4-galactosyl-transferase, β-1,3-N-acetylgalactosaminyl-transferase, β-1,3-glucuronosyl-transferase, α-2,3-sialyl-transferase, α-2,6-sialyl-transferase, α-2,8-sialyl-transferase, α-1,2-fucosyl-transferase, α-1,3-fucosyl-transferase and α-1,4-fucosyl-transferase. More preferably, the glycosyl transferases are selected from β-1,3-N-acetylglucosaminyl transferase, β-1, 6-N-acetylglucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and α-1,4 fucosyl transferase, that is from those involved in the construction of HMO core structures as well as fucosylated and/or sialylated HMOs and its glycosidic derivatives, wherein the aglycon is a moiety defined above at the group of carbohydrate acceptors. The genes encoding the above-mentioned transferases have been described in the literature.

In the glycosyl transferase mediated glycosylation processes of this invention, activated sugar nucleotides serve as donors. Each activated sugar nucleotide generally comprises a phosphorylated glycosyl residue attached to a nucleoside, and the specific glycosyl transferase enzyme accepts only the specific sugar nucleotide. Thus, preferably the following activated sugar nucleotides are involved in the glycosyl transfer: UDP-Glc, UDP-Gal, UDP-GlcNAc, UDP-GalNAc, UDP-glucuronic acid, UDP-Xyl, GDP-Man, GDP-Fuc and CMP-sialic acid, particularly those selected from the group consisting of UDP-Gal, UDP-GlcNAc, GDP-Fuc and CMP-sialic acid.

The genetically modified microorganism used in the process of this invention possesses a biosynthetic pathway to the above mentioned activated sugar nucleotides, that is, it has one or more sets of genes encoding one or more enzymes responsible for the synthesis of one or more activated glycosyl nucleotides, ready for glycosylation in glycosyl transferase mediated reaction in the cell, when cultured. The sets of genes are either naturally present in the cell or introduced into the cell by means of recombinant DNA manipulation techniques. The production of the activated glycosyl nucleotides by the cell takes place under the action of enzymes involved in the biosynthetic pathway of that respective sugar nucleotide stepwise reaction sequence starting from a carbon source (for a review for monosaccharide metabolism see e.g. H. H. Freeze and A. D. Elbein: *Chapter 4: Glycosylation precursors*, in: Essentials of Glycobiology, $2^{nd}$ edition (Eds. A. Varki et al.), Cold Spring Harbour Laboratory Press (2009)).

It should be emphasized, that the production of the activated sugar nucleotides by the genetically modified microorganism via its own biosynthetic pathway is advantageous compared to in vitro versions of transfer glycosylation, as it avoids using the very expensive sugar nucleotide type donors added exogenously, hence the donors are formed by the cell in situ and the phosphatidyl nucleoside leaving groups are recycled in the cell.

In addition, the microorganism used in the process of the invention comprises genes encoding a sucrose utilization system, that is the cell has a capability to catabolically utilize sucrose as a carbon source, as well as an energy source. The system that enables the cell to utilize sucrose can be one normally found in the gene pool of that cell but preferably is a heterologous system (i.e. derived from a different organism and transferred to the host cell by conventional recombinant DNA manipulation techniques, preferably via an expression vector). Typically two kinds of sucrose catabolism can be used. According to the phosphoenolpyruvate (PEP)-dependent phosphotransferase system ("PTS"), sucrose is transported into the microorganism and concomitantly phosphorylated to generate intracellular sucrose-6-phosphate which is hydrolysed to glucose-6-phosphate and fructose that are then involved in the central carbon metabolism of the cell. PTS can be encoded by scr or sac genes. According to non-phosphotransferase-dependent system ("non-PTS"), extracellular sucrose enters the cell with the aid of a proton symport transport system (sucrose permease) and, after transport, is hydrolysed by an invertase enzyme to glucose and fructose followed by phosphorylation. In this regard, the csc regulon consists of genes encoding the enzymes that are responsible for the non-PTS sucrose utilization.

During fermentation in the process of this invention, the oligosaccharide-producing microorganism is fed with sucrose that provides energy via glycolysis for growing, reproducing and maintaining its structure. In addition, the sucrose taken up by the cell provides, via sucrose catabolism, precursors for the synthesis of the activated sugar nucleotide(s) necessary for the glycosylation process that takes place in the cell. The internalized carbohydrate acceptor participates in the glycosyl transferase induced glycosylation reaction, in which a glycosyl residue of an activated nucleotide donor produced by the cell is transferred so that the acceptor is glycosylated. Optionally, when more than one glycosyl transferase is expressed by the cell, additional glycosylation reactions can occur resulting in the formation of the target oligosaccharide. Of course, the cell preferably lacks any enzyme activity which would degrade the oligosaccharide derivatives produced in the cell.

In a preferred realization of the process for making an oligosaccharide product, the sucrose utilization system is heterologous. This is the case when the microorganism, preferably a bacterium, more preferably an $E.\ coli$, is a strain that is optimized for an industrially profitable transformation like oligosaccharide production, because such a strain generally has no ability to utilize sucrose. Therefore, a sucrose uptake cassette should be introduced, using an appropriate expression plasmid or via chromosome integration, in the sucrose minus cell to make it be sucrose plus. More preferably, the sucrose pathway genes comprise a PTS-dependent sucrose utilization system, and especially the source regulon is scr. Microorganisms having scr genes are for example $Salmonella$ ssp., Klebsellia pneumonia, $Bacteroides\ fragilis$, $Vibrio\ alginolyticus$.

The scr genes comprise the following: scrY, scrA, scrB and scrR. The gene scrA codes for the sucrose transport protein Enzyme $II^{Scr}$ that provides intracellular sucrose-6-phosphate from extracellular sucrose via an active transport through the cell membrane and the concomitant phosphorylation. The sucrose specific ScrY porin (encoded by scrY) facilitate the sucrose diffusion through the outer membrane. The ScrB invertase enzyme (encoded by scrB) splits the accumulated sucrose-6-phosphate by hydrolysis to glucose-6-phosphate and fructose. Optionally, a fructokinase ScrK (encoded by scrK) phosphorylates fructose to fructose-6-phosphate, however the presence of this enzyme is not crucial because the fructose can be phosphorylated by other mechanisms owned by the cell. The repressor protein ScrR (encoded by scrR) negatively controls the expression of the scrYAB genes and is induced by sucrose or fructose. The expression of the sucrose genes are repressed in the presence of glucose.

In a preferred embodiment, the heterologous scr genes are introduced into the microorganism using plasmids, more preferably by a two-plasmid system where one contains the scrA gene and the other does the scrB gene. The scrY, scrR and optionally the scrK gene can be carried by either plasmids.

Also preferably, antibiotics are not added to the fermentation broth in the process of this invention.

The carbohydrate acceptor to be glycosylated by the microorganism in the process of the invention can be a mono- or disaccharide selected from galactose, N-acetylglucosamine, a galactosylated monosaccharide, an N-acetylglucosaminylated monosaccharide, and glycosidic derivatives thereof defined above. All these carbohydrate derivatives can be easily taken up by a cell having a LacY permease by means of an active transport and accumulate in the cell before being glycosylated (WO 01/04341, Fort et al. $J.\ Chem.\ Soc.,\ Chem.\ Comm.$ 2558 (2005), EP-A-1911850, WO 2013/182206, WO 2014/048439). This is because the cell is able to transport these carbohydrate acceptors into the cell using its LacY permease, and the cell lacks any enzymes that could degrade these acceptors, especially LacZ. Preferably the cell has a deleted or deficient lacA gene on the lac operon.

According to another preferred embodiment, the lacI gene for the lac repressor is also deleted in the microorganism. In the absence of the functioning repressor, no inducer is needed for expressing LacY.

According to another preferred embodiment, a genetically modified cell, particularly a LacZ$^-$Y$^+$ $E.\ coli$ cell, is cultured in an aqueous culture medium in the following phases:

(a) an exponential cell growth phase ensured by sucrose, and then (b) a feeding phase with sucrose which is added continuously ensuring a limited cell growth.

During the feeding phase, the exogenous carbohydrate acceptor, preferably lactose, to be internalized by and glycosylated in the cell, can be added to the culture medium at once, sequentially or continuously. The acceptor can be added in this second phase as a pure solid/liquid or in a form of a concentrated aqueous solution or suspension. The oligosaccharide production takes place in this second phase and can take up to 6-7 days. Preferably, this feeding phase is performed under conditions allowing the production of a culture with a high cell density.

A feature of the process of this invention is that there is no need to change the carbon source and/or the energy source between the growth phase and the production phase of the microorganism.

Optionally, the process further comprises the addition of an inducer to the culture medium to induce the expression in the cell of enzyme(s) and/or of protein(s) involved in the transport of the acceptor and/or in the glycosylation of the internalized acceptor and/or in the biosynthesis of the activated sugar nucleotide donors. The inducer is preferably isopropyl β-D-thiogalactoside (IPTG) and is added to the culture medium in the beginning of the feeding phase. However, the use of inducer is not necessary if the cell is of LacI$^-$ phenotype.

It is believed that the microorganisms described above are highly stable under the process conditions of this invention described above. As a result, it is believed that these microorganisms can be used to produce oligosaccharides using sucrose as their carbon and energy sources at least at the same production rate as, and in a more reliable and reproducible manner than, like microorganisms using glycerol and/or glucose as their carbon and/or energy sources. In this regard, one or more plasmids, preferably one or two plasmids, containing the scr genes (needed by the microorganisms for utilizing sucrose) plus one or more glycosyl transferase genes (needed by the microorganisms for making an exogenous oligosaccharide) are particularly stable in the above described microorganisms over fermentation periods of more than 4 days, preferably 5 to 7 days.

At the end of the second phase, the oligosaccharide product has accumulated both in the intra- and the extracellular matrix of the microorganism. The product is then preferably transported out of the cell to the supernatant in a passive way, i.e., it can diffuse outside across the cell membrane. This transport can be facilitated by one or more sugar efflux transporters in the cell, i.e. proteins that promote the effluence of sugar derivatives from the cell to the supernatant. The sugar efflux transporter(s) can be present exogenously or endogenously and can be overexpressed under the conditions of the fermentation to enhance the export of the oligosaccharide derivative produced. The specificity towards the sugar moiety of the product to be secreted can be altered by mutation of the cell by means of conventional recombinant DNA manipulation techniques. Preferably, the oligosaccharide accumulates in the extracellular matrix. Alternatively, the oligosaccharide can be transported out of the cell to the supernatant by disrupting the cell walls in a conventional manner.

The oligosaccharide product can then be separated in a conventional manner from the aqueous culture medium, in which it was made by the cell.

A first step of separating the oligosaccharide from the culture medium preferably involves separating the oligosaccharide from the microorganism which produced it. This preferably involves clarifying the culture medium to remove suspended particulates and contaminants, particularly cells, cell components, insoluble metabolites and debris produced by culturing the genetically modified microorganism. In this step, the aqueous culture medium, which contains the oligosaccharide product, can be clarified in a conventional manner. Preferably, the culture medium is clarified by centrifugation and/or filtration.

A second step of separating the oligosaccharide from the culture medium preferably involves removing substantially all the proteins, as well as peptides, amino acids, RNA and DNA and any endotoxins and glycolipids that could interfere with the subsequent separation step, from the aqueous culture medium, preferably after it has been clarified. In this step, proteins and related impurities can be removed from the culture medium in a conventional manner. Preferably, proteins and related impurities are removed from the culture medium by ultrafiltration, tangential flow high-performance filtration, tangential flow ultrafiltration, affinity chromatography, ion exchange chromatography, hydrophobic interaction chromatography and/or gel filtration (i.e., size exclusion chromatography), particularly by chromatography, more particularly by ion exchange chromatography or hydrophobic interaction chromatography. With the exception of size exclusion chromatography, proteins and related impurities are retained by a chromatography medium or a selected membrane, while the oligosaccharide product remains in the aqueous culture medium.

If desired, the oligosaccharide product in the aqueous culture medium can then be separated from sugar-like by-product(s) and from the culture medium, after proteins and related impurities have been removed from the culture medium. This can be suitably done by subjecting the culture medium to chromatographic separation. This separation can be carried out, in case of a neutral oligosaccharide product, in a chromatographic separation column, filled with a conventional acidic cationic ion exchange resin. The acidic cationic ion exchange resin can be in monovalent or divalent cationic form and is preferably in $H^+$, $K^+$, $Na^+$, $Mg^{2+}$ or $Ca^{2+}$ form, particularly $Ca^{2+}$. The chromatographic separation can be carried out in a conventional manner at a pH of the solution of 2 to 9. The eluent used in the chromatographic separation is preferably water, especially demineralized water, but aqueous salt solutions can also be used. Alcohols, such as ethanol, and aqueous alcohol mixtures can also be used.

According to a preferred embodiment, the process of this invention for producing an oligosaccharide, preferably having a lactose unit at the reducing end or a glycoside thereof comprises the steps of:

(i) providing a genetically modified cell comprising
    a recombinant gene encoding a glycosyl transferase enzyme which is able to transfer the glycosyl residue of an activated sugar nucleotide to the internalized lactose or glycoside thereof,
    a biosynthetic pathway to the activated sugar nucleotide, (ii) culturing the genetically modified cell in the presence of the exogenous lactose or glycoside thereof and sucrose inducing
    internalization of the exogenous lactose or glycoside thereof via an active transport mechanism by the genetically modified cell, and
    formation of the oligosaccharide having a lactose unit at the reducing end or a glycoside thereof from the internalized lactose or glycoside thereof by a glycosyl transfer mediated by the glycosyl transferase enzyme expressed by the cell, (iii) isolating the oligosaccharide product from the cell, from the culture medium or from both,
    characterized in that the cell also comprises a heterologous sucrose utilization system, preferably a PTS-dependent sucrose utilization system, especially where the source regulon is scr, to provide sucrose as a carbon source for biosynthesis of said activated sugar nucleotide by said cell.

The genetically modified cell, used in this preferred process, can have more than one recombinant gene, encoding more than one glycosyl transferase enzyme which is able to transfer the glycosyl residue of an activated sugar nucleotide to an internalized acceptor molecule or the previously glycosylated acceptor made by the same cell, so the oligosaccharide product is formed from the internalized acceptor by multiple glycosyl transfer mediated by multiple glycosyl transferases expressed by the cell. Accordingly, the resulting oligosaccharide product can be a glycosylated lactose or a glycoside thereof. The glycosylated lactose is preferably an N-acetyl-glucosaminylated, galactosylated, fucosylated and/or sialylated lactose. In order to produce these derivatives the cell comprises one or more recombinant genes encoding an N-acetyl-glucosaminyl transferase, a galactosyl transferase, a sialyl transferase and/or a fucosyl transferase, and also comprise a biosynthetic pathway to the corresponding activated sugar type nucleotides, that is UDP-GlcNAc, UDP-Gal, GDP-Fuc and/or CMP-sialic acid.

More preferably, the oligosaccharide product made by this process is characterized by formula 1

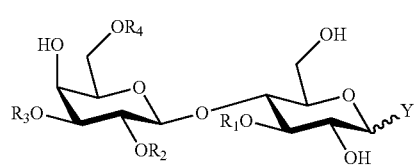

wherein Y is OH or a non-sugar aglycon defined above, preferably OH,
R₁ is fucosyl or H,
R₂ is fucosyl or H,
R₃ is selected from H, sialyl, N-acetyl-lactosaminyl and lacto-N-biosyl groups, wherein the N-acetyl-lactosaminyl group can carry a glycosyl residue comprising one or more N-acetyl-lactosaminyl and/or one or more lacto-N-biosyl groups; each of the N-acetyl-lactosaminyl and lacto-N-biosyl groups can be substituted with one or more sialyl and/or fucosyl residue,
R₄ is selected from H, sialyl and N-acetyl-lactosaminyl groups optionally substituted with a glycosyl residue comprising one or more N-acetyl-lactosaminyl and/or one or more lacto-N-biosyl groups; each of the N-acetyl-lactosaminyl and lacto-N-biosyl groups can be substituted with one or more sialyl and/or fucosyl residue,
provided that at least one of the $R_1$, $R_2$, $R_3$ and $R_4$ groups is different from H.

Even more preferably, the compound of formula 1 made by this process can be characterized by formula 1a, 1b or 1c

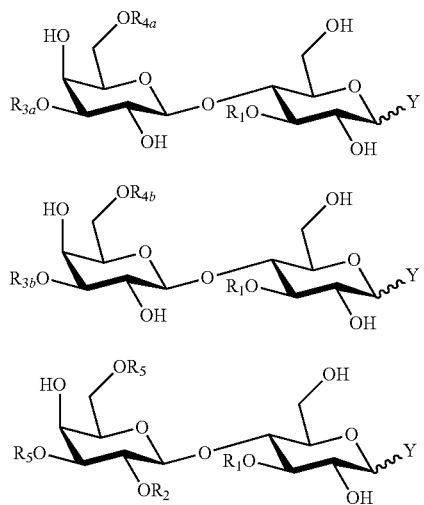

wherein Y, $R_1$ and $R_2$ are as defined above, preferably OH,
$R_{3a}$ is an N-acetyl-lactosaminyl group optionally substituted with a glycosyl residue comprising one N-acetyl-lactosaminyl and/or one lacto-N-biosyl group; each of the N-acetyl-lactosaminyl and lacto-N-biosyl groups can be substituted with one or more sialyl and/or fucosyl residue,
$R_{4a}$ is H or an N-acetyl-lactosaminyl group optionally substituted with a lacto-N-biosyl group; each of the N-acetyl-lactosaminyl and lacto-N-biosyl groups can be substituted with one or more sialyl and/or fucosyl residue,
$R_{3b}$ is a lacto-N-biosyl group optionally substituted with one or more sialyl and/or fucosyl residue(s),
$R_{4b}$ is H or an N-acetyl-lactosaminyl group optionally substituted with one or two N-acetyl-lactosaminyl and/or one lacto-N-biosyl groups; each of the N-acetyl-lactosaminyl and lacto-N-biosyl groups can be substituted with one or more sialyl and/or fucosyl residues,
$R_5$ is, independently, H or sialyl,
and wherein at least one of $R_1$, $R_2$ or $R_5$ is not H.

Still more preferably, the compounds according to formulae 1a or 1b made by this process are characterized in that:
the N-acetyl-lactosaminyl group in the glycosyl residue of $R_{3a}$ is attached to another N-acetyl-lactosaminyl group with a 1-3 interglycosidic linkage,
the lacto-N-biosyl group in the glycosyl residue of $R_{3a}$ is attached to the N-acetyl-lactosaminyl group with a 1-3 interglycosidic linkage,
the lacto-N-biosyl group in the glycosyl residue of $R_{4a}$ is attached to the N-acetyl-lactosaminyl group with a 1-3 interglycosidic linkage,
the N-acetyl-lactosaminyl group in the glycosyl residue of $R_{4b}$ is attached to another N-acetyl-lactosaminyl group with a 1-3 or a 1-6 interglycosidic linkage,
the lacto-N-biosyl group in the glycosyl residue of $R_{4b}$ is attached to the N-acetyl-lactosaminyl group with a 1-3 interglycosidic linkage.

Yet more preferably, the compounds according to formulae 1a, 1b and 1c made by the process are human milk oligosaccharides (when Y is OH) or glycosides thereof (when Y is non-sugar aglycon).

The preferred compounds of formula 1a made by the process are selected from lacto-N-neotetraose, para-lacto-N-hexaose, para-lacto-N-neohexaose, lacto-N-neohexaose, para-lacto-N-octaose, lacto-N-neooctaose and glycosides thereof, all of which can optionally be substituted with one or more sialyl and/or fucosyl residue. The preferred compounds of formula 1b made by the process is selected from lacto-N-tetraose, lacto-N-hexaose, lacto-N-octaose, iso-lacto-N-octaose, lacto-N-decaose, lacto-N-neodecaose and glycosides thereof, all of them can optionally be substituted with one or more sialyl and/or fucosyl residue.

Particularly preferred compounds of formula 1a or 1b are characterized in that:
the fucosyl residue attached to the N-acetyl-lactosaminyl and/or the lacto-N-biosyl group is linked to
the galactose of the lacto-N-biosyl group with 1-2 interglycosidic linkage and/or
the N-acetyl-glucosamine of the lacto-N-biosyl group with 1-4 interglycosidic linkage and/or
the N-acetyl-glucosamine of the N-acetyl-lactosaminyl group with 1-3 interglycosidic linkage,
the sialyl residue attached to the N-acetyl-lactosaminyl and/or the lacto-N-biosyl group is linked to
the galactose of the lacto-N-biosyl group with 2-3 interglycosidic linkage and/or
the N-acetyl-glucosamine of the lacto-N-biosyl group with 2-6 interglycosidic linkage and/or
the galactose of the N-acetyl-lactosaminyl group with 2-6 interglycosidic linkage.

According to the most preferred aspect, the compounds of subformulae 1a, 1b or 1c are selected from the group of: 2'-fucosyllactose, 3-fucosyllactose, 2',3-difucosyllactose, 3'-sialyllactose, 6'-sialyllactose, 3'-sialyl-3-fucosyllactose, lacto-N-tetraose, lacto-N-neotetraose, LNFP-I, LNFP-II, LNFP-III, LNFP-V, LST-a, LST-b, LST-c, FLST-a, FLST-b, FLST-c, LNDFH-I, LNDFH-II, LNDFH-III, DS-LNT, FDS-LNT I, FDS-LNT II and their glycosides, or salts thereof. The glycosides can be alpha or beta-anomers, but preferably beta-anomers.

The preferred carbohydrate acceptor, exogenously added to the culture medium, is lactose, and the preferred oligosaccharide product is a human milk oligosaccharide (HMO). The HMOs consist of a lactose unit at the reducing end and one or more from the following monosaccharide units: N-acetyl-glucosamine, galactose, fucose and sialic acid (see Urashima et al.: *Milk Oligosaccharides*, Nova Biomedical Books, New York, 2011, ISBN: 978-1-61122-831-1). In order to produce HMOs the cell then comprises one or more recombinant genes encoding β-1,3-N-acetyl-glucosaminyl transferase, β-1,6-N-acetyl-glucosaminyl transferase, β-1,3-galactosyl transferase, β-1,4-galactosyl transferase, α-2,3-sialyltransferase, α-2,6-sialyl transferase, α-1,2-fucosyl transferase, α-1,3-fucosyl transferase and/or α-1,4 fucosyl transferase, and also comprise a biosyntethic pathway to the corresponding activated sugar type nucleotides, that is UDP-GlcNAc, UDP-Gal, GDP-Fuc and/or CMP-sialic acid.

According to another preferred embodiment, the process of this invention for producing an N-acetyled HMO, preferably of 3-5 monosaccharide units, comprises the steps of:
(i) providing a genetically modified *E. coli* cell of LacZ$^-$, LacY$^+$ genotype or LacZ$^-$, LacY$^+$, LacI$^-$ genotype, comprising:
   a recombinant gene encoding an N-acetyl-glucosaminyl transferase enzyme which is able to transfer the GlcNAc of UDP-GlcNAc to the internalized lactose,
   optionally a recombinant gene encoding a galactosyl transferase enzyme which is able to transfer the galactosyl residue of UDP-Gal to the N-acetyl-glucosaminylated lactose, and
   one or more genes encoding a biosynthetic pathway to UDP-GlcNAc and optionally to UDP-Gal,
(ii) culturing the genetically modified *E. coli* cell of LacZ$^-$, LacY$^+$ genotype or LacZ$^-$, Lac$^+$, LacI$^-$ genotype, in the presence of exogenous lactose and sucrose, thereby inducing:
   internalization of the exogenous lactose via an active transport mechanism by the cell, and
   formation, within the cell, of an N-acetyl-glucosaminylated lactose that is optionally galactosylated, and then
(iii) separating the N-acetyl-glucosaminylated lactose, that is optionally galactosylated, from the cell, from the culture medium or from both,
   characterized in that the cell also comprises a heterologous PTS-dependent sucrose utilization system to provide sucrose as a carbon source, as well as an energy source, for biosynthesis of UDP-GlcNAc and optionally UDP-Gal by the cell.

The heterologous PTS-dependent sucrose utilization system preferably comprises scr genes, more preferably scrY, scrA, scrB and scrR, and particularly does not contain scrK.

If the N-acetyl-glucosaminyl transferase is a β-1,3-N-acetyl-glucosaminyl transferase and no recombinant gene encoding a galactosyl transferase is present in the cell, the product is preferably lacto-N-triose, and if a β-1,3- or a β-1,4-galactosyl transferase is also present in the cell, the product is preferably LNT or LNnT, respectively.

According to yet another preferred embodiment, the process of this invention for producing a fucosylated HMO, preferably of 3-5 monosaccharide units, comprises the steps of:
(i) providing a genetically modified *E. coli* cell of LacZ$^-$, LacY$^+$ genotype or LacZ$^-$, LacY$^+$, LacI$^-$ genotype, comprising:
   a recombinant gene encoding a fucosyl transferase enzyme which is able to transfer the fucosyl residue of GDP-Fuc to the internalized lactose, and
   one or more genes encoding a biosynthetic pathway to GDP-Fuc,
(ii) culturing the cell in the presence of exogenous lactose and sucrose, thereby inducing:
   internalization of the exogenous lactose via an active transport mechanism by the genetically modified cell, and
   formation of a fucosylated lactose, and then
(iii) separating the fucosylated lactose product from the cell, from the culture medium or from both,
   characterized in that the cell also comprises a heterologous PTS-dependent sucrose utilization system to provide sucrose as a carbon source, as well as an energy source, for biosynthesis of GDP-Fuc by the cell. Preferably, in this process, the culturing step comprises a two-step feeding, with a second feeding phase by continuously adding to the culture an amount of sucrose that is less than that added continuously in a first feeding phase so as to slow the cell growth and increase the content of product produced in the high cell density culture. The feeding rate of sucrose added continuously to the cell culture during the second feeding phase is around 30-40% less than that of sucrose added continuously during the first feeding phase. During both feeding phases, lactose can be added continuously, preferably with sucrose in the same feeding solution, or sequentially. Optionally, the culturing further comprises a third feeding phase when considerable amount of unused acceptor remained after the second phase in the extracellular fraction. Then the addition is sucrose is continued without adding the acceptor, preferably with around the same feeding rate set for the second feeding phase until consumption of the acceptor.

The heterologous PTS-dependent sucrose utilization system preferably comprises scr genes, more preferably scrY, scrA, scrB and scrR, and particularly does not contain scrK.

If the fucosyl transferase is an α-1,2-fucosyl transferase, the product is preferably 2'-fucosyllactose, if the fucosyl transferase is an α-1,3-fucosyl transferase, the product is preferably 3-fucosyllactose, and if both α-1,2- and α-1,3-fucosyl transferases are expressed in the cell, the product is preferably difucosyllactose.

According to still another preferred embodiment, the process of this invention for producing a sialylated HMO, preferably of 3-5 monosaccharide units, comprises the steps of:
(i) providing a genetically modified *E. coli* cell of LacZ$^-$, Lac$^+$ genotype or LacZ$^-$, Lac$^+$, LacI$^-$ genotype, comprising:
   a recombinant gene encoding a sialyl transferase enzyme which is able to transfer the sialyl residue of CMP-sialic acid to the internalized lactose, and
   one or more genes encoding a biosynthetic pathway to CMP-sialic acid,
(ii) culturing the genetically modified *E. coli* cell of LacZ$^-$, Lac$^+$ genotype or LacZ$^-$, Lac$^+$, LacI$^-$ genotype, in the presence of exogenous lactose and sucrose, thereby inducing:
   internalization of the exogenous lactose via an active transport mechanism by the genetically modified cell, and
   formation of a sialylated lactose, and then
(iii) separating the sialylated lactose from the cell, from the culture medium or from both,
   characterized in that the cell also comprises a heterologous PTS-dependent sucrose utilization system to provide sucrose as a carbon source, as well as an energy source, for biosynthesis of CMP-sialic acid by the cell.

The heterologous PTS-dependent sucrose utilization system preferably comprises scr genes, more preferably scrY, scrA, scrB and scrR, and particularly does not contain scrK.

If the sialyl transferase is an α-2,3-sialyl transferase, the product is preferably 3'-sialyllactose, and if the sialyl transferase is an α-2,6-sialyl transferase, the product is preferably 6'-sialyllactose.

According to another preferred embodiment, the process of this invention for producing a fucosylated and sialylated HMO, preferably of 3-5 monosaccharide units, comprises the steps of:

(i) providing a genetically modified *E. coli* cell of LacZ$^-$, Lac$^+$ genotype or LacZ$^-$, Lac$^+$, LacI$^-$ genotype, comprising:
  a recombinant gene encoding a sialyl transferase enzyme which is able to transfer the sialyl residue of CMP-sialic acid to the internalized lactose or previously fucosylated lactose,
  a recombinant gene encoding a fucosyl transferase enzyme which is able to transfer the fucosyl residue of GDP-Fuc to the internalized lactose or previously sialylated lactose, and
  one or more genes encoding a biosynthetic pathway to CMP-sialic acid and GDP-Fuc, (ii) culturing the genetically modified *E. coli* cell of LacZ$^-$, Lac$^+$ genotype or LacZ$^-$, Lac$^+$, LacI$^-$ genotype, in the presence of exogenous lactose and sucrose, thereby inducing:
  internalization of the exogenous lactose via an active transport mechanism by the genetically modified cell, and
  formation of a sialyl-fucosyl-lactose, and then (iii) separating the sialyl-fucosyl-lactose from the cell, from the culture medium or from both,
  characterized in that the cell also comprises a heterologous PTS-dependent sucrose utilization system to provide sucrose as a carbon source, as well as an energy source, for biosynthesis of CMP-sialic acid and GDP-Fuc by the cell.

The heterologous PTS-dependent sucrose utilization system preferably comprises scr genes, more preferably scrY, scrA, scrB and scrR, and particularly does not contain scrK.

If the sialyl transferase is an α-2,3-sialyltransferase and the fucosyl transferase is an α-1,3-fucosyl transferase, the product is preferably 3'-sialyl-3-fucosyllactose.

A second aspect of the invention relates to providing a genetically modified microorganism that can internalize sucrose and a carbohydrate acceptor, which is not sucrose, preferably lactose, into said microorganism and that comprises:
  a recombinant gene encoding a glycosyl transferase which can transfer a glycosyl residue of an activated sugar nucleotide to the acceptor within the microorganism,
  a biosynthetic pathway for making the activated sugar nucleotide from sucrose, and
  one or more genes encoding a heterologous PTS-dependent sucrose utilization system, preferably scr genes, so that said cell can use sucrose as a carbon source, preferably the main carbon source, more preferably the sole carbon source, for making said activated sugar nucleotide and as an energy source, preferably the main energy source, more preferably the sole energy source, for making said oligosaccharide.

The genetically modified microorganism of the second aspect can be selected from the group consisting of bacteria and yeasts, preferably a bacterium. Bacteria are preferably selected from the group of: *Escherichia coli*, *Bacillus* spp. (e.g. *Bacillus subtilis*), *Campylobacter pylori*, *Helicobacter pylori*, *Agrobacterium tumefaciens*, *Staphylococcus aureus*, *Thermophilus aquaticus*, *Azorhizobium caulinodans*, *Rhizobium leguminosarum*, *Neisseria gonorrhoeae*, *Neisseria meningitis*, *Lactobacillus* spp., *Lactococcus* spp., *Enterococcus* spp., *Bifidobacterium* spp., *Sporolactobacillus* spp., *Micromomospora* spp., *Micrococcus* spp., *Rhodococcus* spp., *Pseudomonas*, among which *E. coli* is preferred.

Moreover, the genetically modified cell of the second aspect comprises one or more endogenous or recombinant genes encoding one or more glycosyl transferase enzymes that are able to transfer the glycosyl residue of an activated sugar nucleotide to the internalized acceptor. The origin of the heterologous nucleic acid sequence can be any animal (including human) or plant, eukaryotic cells such as those from *Saccharomyces cerevisae*, *Saccharomyces pombe*, *Candida albicans* or from algae, prokaryotic cells such as those originated from *E. coli*, *Bacteroides fragilis*, *Photobacterium* sp., *Bacillus subtilis*, *Campylobacter pylori*, *Helicobacter pylori*, *Agrobacterium tumefaciens*, *Staphylococcus aureus*, *Thermophilus aquaticus*, *Azorhizobium caulinodans*, *Rhizobium leguminosarum*, *Rhizobium meliloti*, *Neisseria gonorrhoeae* and *Neisseria meningitidis*, or virus. The glycosyl transferase enzyme/enzymes expressed by the protein(s) encoded by the gene(s) or equivalent DNA sequence(s) are preferably glucosyl transferases, galactosyl transferases, N-acetylglucosaminyl transferases, N-acetylgalactosaminyl transferases, glucuronosyl transferases, xylosyl transferases, mannosyl transferases, fucosyl transferases, sialyl transferases and the like. In a preferred embodiment, the glycosyl transferases are selected from the group consisting of β-1,3-N-acetylglucosaminyl-transferase, β-1,6-N-acetylglucosaminyl-transferase, β-1,3-galactosyl-transferase, β-1,4-galactosyl-transferase, β-1,3-N-acetylgalactosaminyl-transferase, β-1,3-glucuronosyl-transferase, α-2,3-sialyl-transferase, α-2,6-sialyl-transferase, α-2,8-sialyl-transferase, α-1,2-fucosyl-transferase, α-1,3-fucosyl-transferase and α-1,4-fucosyl-transferase. More preferably, the glycosyl transferases are selected from β-1,3-N-acetylglucosaminyl transferase, β-1,6-N-acetylglucosaminyl transferase, β-1,3-galactosyl transferase, β-1,4-galactosyl transferase, α-2,3-sialyl transferase, α-2,6-sialyl transferase, α-1,2-fucosyl transferase, α-1,3-fucosyl transferase and α-1,4 fucosyl transferase, that is from those involved in the construction of HMO core structures as well as fucosylated and/or sialylated HMOs and its glycosidic derivatives, wherein the aglycon is a moiety defined above at the group of carbohydrate acceptors.

Furthermore, the genetically modified microorganism of the second aspect of the invention involves a transporting system that internalize the exogenous carbohydrate acceptor, preferably lactose, into the microorganism for glycosylation and to produce a foreign oligosaccharide of interest, preferably without adversely affecting the basic functions of the microorganism or destroying its integrity. Preferably, the carbohydrate acceptor is internalized with the aid of an active transport, mediated by a transporter protein, called permease, which act as enzymes and with which the microorganism is able to admit exogenous substances and to concentrate them in the cytoplasm. Specifically, lactose permease (LacY) acts specifically on galactose, simple galactosyl disaccharides such as lactose and their glycosides. The genetically modified microorganism preferably lacks any enzyme activity (such as LacZ) that would degrade the acceptor. Likewise, the microorganism is not able to hydrolyze or degrade the oligosaccharide product.

In addition, the genetically modified microorganism of the second aspect comprises genes encoding a the phosphoenolpyruvate (PEP)-dependent phosphotransferase (PTS) sucrose utilization system, that is the cell has a capability to catabolically utilize sucrose as a carbon source, as well as an energy source. The PTS-system is heterologous (i.e. derived from a different organism and transferred to the host cell by conventional recombinant DNA manipulation techniques, preferably via an expression vector) and can be encoded by scr or sac genes, preferably scr genes.

Preferably scr genes comprised by the genetically modified microorganism, preferably *E. coli*, are the following: scrY, scrA, scrB and scrR. The gene scrA codes for the sucrose transport protein Enzyme II$^{Scr}$ that provides intracellular sucrose-6-phosphate from extracellular sucrose via an active transport through the cell membrane and the concomitant phosphorylation. The sucrose specific ScrY porin (encoded by scrY) facilitate the sucrose diffusion through the outer membrane. The ScrB invertase enzyme (encoded by scrB) splits the accumulated sucrose-6-phosphate by hydrolysis to glucose-6-phosphate and fructose. The presence of a fructokinase ScrK (encoded by scrK) is not crucial because the fructose can be phosphorylated by other mechanisms owned by the cell. The repressor protein ScrR (encoded by scrR) negatively controls the expression of the scrYAB genes and is induced by sucrose or fuctose.

In a preferred embodiment, the heterologous scr genes are introduced into the microorganism using plasmids, more preferably by a two-plasmid system where one contains the scrA gene and the other does the scrB gene. The scrY and scrR can be carried by either plasmids.

Preferably the genetically modified microorganism of the second aspect has a deleted or deficient lacA gene on the lac operon.

Also preferably, the lacI gene for the lac repressor is also deleted in the genetically modified microorganism.

The genetically modified microorganism disclosed above is suitable for preparing, from lactose or lactosides having an aglycon disclosed above, an oligosaccharide of formula 1

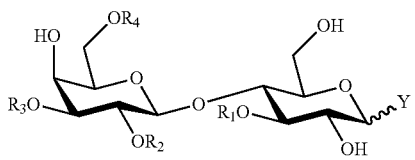

wherein Y is OH or a non-sugar aglycon defined above, preferably OH,
$R_1$ is fucosyl or H,
$R_2$ is fucosyl or H,
$R_3$ is selected from H, sialyl, N-acetyl-lactosaminyl and lacto-N-biosyl groups, wherein the N-acetyl-lactosaminyl group can carry a glycosyl residue comprising one or more N-acetyl-lactosaminyl and/or one or more lacto-N-biosyl groups; each of the N-acetyl-lactosaminyl and lacto-N-biosyl groups can be substituted with one or more sialyl and/or fucosyl residue,
$R_4$ is selected from H, sialyl and N-acetyl-lactosaminyl groups optionally substituted with a glycosyl residue comprising one or more N-acetyl-lactosaminyl and/or one or more lacto-N-biosyl groups; each of the N-acetyl-lactosaminyl and lacto-N-biosyl groups can be substituted with one or more sialyl and/or fucosyl residue,
provided that at least one of the $R_1$, $R_2$, $R_3$ and $R_4$ groups is different from H.

Preferably, the oligosaccharide of formula 1 is a human milk oligosaccharide (when Y is OH) or a glycosides thereof (when Y is non-sugar aglycon), more preferably a human milk oligosaccharide.

According to a preferred embodiment, the genetically modified microorganism is an *E. coli* cell of LacZ$^-$, Lac$^+$ genotype or LacZ$^-$, Lac$^+$, LacI$^-$ genotype, and comprises:
a recombinant gene encoding an N-acetyl-glucosaminyl transferase enzyme which is able to transfer the GlcNAc of UDP-GlcNAc to the internalized lactose,
optionally a recombinant gene encoding a galactosyl transferase enzyme which is able to transfer the galactosyl residue of UDP-Gal to the N-acetyl-glucosaminylated lactose,
one or more genes encoding a biosynthetic pathway to UDP-GlcNAc and optionally to UDP-Gal, and
a heterologous PTS-dependent sucrose utilization system comprising scrY, scrA, scrB and scrR genes to provide sucrose as a carbon source, as well as an energy source, for biosynthesis of UDP-GlcNAc and optionally UDP-Gal produced by the cell.

The heterologous scr cluster particularly does not contain scrK.

More preferably, the N-acetyl-glucosaminyl transferase is a β-1,3-N-acetyl-glucosaminyl transferase and no recombinant gene encoding a galactosyl transferase is present in the cell. In this case the genetically modified *E. coli* produces primarily lacto-N-triose.

Also more preferably, the N-acetyl-glucosaminyl transferase is a β-1,3-N-acetyl-glucosaminyl transferase and galactosyl transferase is a β-1,3-galactosyl transferase. In this case the genetically modified *E. coli* produces primarily LNT.

Yet more preferably, the N-acetyl-glucosaminyl transferase is a β-1,3-N-acetyl-glucosaminyl transferase and galactosyl transferase is a β-1,4-galactosyl transferase. In this case the genetically modified *E. coli* produces primarily LNnT.

According to another preferred embodiment, the genetically modified microorganism is an *E. coli* cell of LacZ$^-$, Lac$^+$ genotype or LacZ$^-$, Lac$^+$, LacI$^-$ genotype, and comprises:
a recombinant gene encoding a fucosyl transferase enzyme which is able to transfer the fucosyl residue of GDP-Fuc to the internalized lactose,
one or more genes encoding a biosynthetic pathway to GDP-Fuc, and
a heterologous PTS-dependent sucrose utilization system comprising scrY, scrA, scrB and scrR genes to provide sucrose as a carbon source, as well as an energy source, for biosynthesis of GDP-fucose produced by the cell.

The heterologous scr cluster particularly does not contain scrK.

More preferably, the fucosyl transferase is an α-1,2-fucosyl transferase. In this case the genetically modified *E. coli* produces primarily 2'-FL.

Also more preferably, the fucosyl transferase is an α-1,3-fucosyl transferase. In this case the genetically modified *E. coli* produces primarily 3-FL.

Yet more preferably, there are two fucosyl transferases present in the cell: an α-1,2-fucosyl transferase and an α-1,3-fucosyl transferase. In this case the genetically modified *E. coli* produces primarily DFL.

According to another preferred embodiment, the genetically modified microorganism is an *E. coli* cell of LacZ$^-$, Lac$^+$ genotype or LacZ$^-$, Lac$^+$, LacI$^-$ genotype, and comprises:
a recombinant gene encoding a sialyl transferase enzyme which is able to transfer the sialyl residue of CMP-sialic acid to the internalized lactose, one or more genes encoding a biosynthetic pathway to CMP-sialic acid, and a heterologous PTS-dependent sucrose utilization system comprising scrY, scrA, scrB and scrR genes to provide sucrose as a carbon source, as well as an energy source, for biosynthesis of CMP-sialic acid produced by the cell.

The heterologous scr cluster particularly does not contain scrK.

More preferably, the sialyl transferase is an α-2,3-sialyl transferase. In this case the genetically modified *E. coli* produces primarily 3'-SL.

Also more preferably, the sialyl transferase is an α-2,6-sialyl transferase. In this case the genetically modified *E. coli* produces primarily 6'-SL.

According to another preferred embodiment, the genetically modified microorganism is an *E. coli* cell of LacZ⁻, Lac⁺ genotype or LacZ⁻, Lac⁺, LacI⁻ genotype, and comprises:

a recombinant gene encoding a sialyl transferase enzyme which is able to transfer the sialyl residue of CMP-sialic acid to the internalized lactose, optionally fucosylated, a recombinant gene encoding a fucosyl transferase enzyme which is able to transfer the fucosyl residue of GDP-Fuc to the internalized lactose, optionally sialylated, one or more genes encoding a biosynthetic pathway to CMP-sialic acid, one or more genes encoding a biosynthetic pathway to GDP-Fuc, and a heterologous PTS-dependent sucrose utilization system comprising scrY, scrA, scrB and scrR genes to provide sucrose as a carbon source, as well as an energy source, for biosynthesis of CMP-sialic acid and GDP-fucose produced by the cell.

The heterologous scr cluster particularly does not contain scrK.

More preferably, the sialyl transferase is an α-2,3-sialyl transferase and the fucosyl transferase is an α-1,3-fucosyl transferase. In this case the genetically modified *E. coli* produces primarily 3'-sialyl-3-fucosyl lactose.

EXAMPLES

Example 1: Comparative Test for Making LNnT by a Glycerol or Sucrose Utilizing *E. coli*

Bacterial Strains:

Both strains were constructed from *Escherichia coli* K12 strain DH1 which was obtained from the Deutsche Sammlung von Mikroorganismen (reference DSM 5346) by deleting the genes: lacZ nanKETA lacA melA wcaJ mdoH, by inserting a Plac promoter, and maintaining genes involved in the UDP-GlcNAc and UDP-Gal biosynthesis. The glycerol utilizing strain (strain I) contains a pBBR3-IgtA-tet plasmid carrying *N. meningitidis* IgtA gene for β-1,3-N-acetylglucosaminyl transfearse and the tetracycline resistant gene, and a pBS-galT-amp plasmid carrying *Helicobacter pylori* galT gene for β-1-4-galactosyl transferase and the ampicillin resistant gene. The sucrose utilizing strain (strain II) contains the two following plasmids:

pBS-scrBR-galT-amp which is a pUC derivative carrying the galT gene encoding an β-1,4-galactosyl transferase, the scrR gene encoding a sucrose repressor, the scrB gene encoding a sucrose-6-phosphate hydrolase and the ampicillin resistance gene;

pBBR3-scrYA-IgtA-tet which is a pBBR1-MCS3 derivative carrying the IgtA gene encoding a β-1,3-N-acetylglucosaminyl transferase, the scrA gene encoding a PTS system sucrose-specific EIIBC component, the scrYgene encoding a sucrose porin and the tetracycline resistance gene.

Fermentation Procedure:

Glucose, glycerol, sucrose and lactose were each sterilized at 120° C. Isopropyl thio-β-D-galactopyranoside (IPTG) was filter sterilized.

The culture was carried out in a 3 l fermenter containing ≈0.9 l of mineral culture medium (Samain et al. *J. Biotechnol.* 72, 33 (1999); does not contain antibiotics for the sucrose system). The temperature was kept at 33° C. and the pH regulated at 6.8 with 28% NH₄OH. The inoculum of the producing strain consisted in a LB medium (20 ml) supplemented with ampicillin and tetracycline for strain I or M9 medium (20 ml) supplemented with sucrose for strain II was added to the fermenter. The exponential growth phase started with the inoculation and stopped until exhaustion of the carbon source (glucose for strain I or sucrose for strain II, ≈17.5 g/l) initially added to the medium. A lactose solution (70 g of lactose/500 ml of water) was then added before starting the feeding with the carbon source (500 g/l solution, 4.5 g/h of glycerol for strain I and 3 g/l of sucrose for strain II). The inducer (isopropyl thio-6-D-galactopyranoside, IPTG, 1-2 ml of a 50 mg/ml solution) was also added. The glycerol-fed fermentation (strain I) lasted for 90 hours after which the cells died (LNnT titre: 45 g/l). The sucrose-fed fermentation (strain II) produced an LNnT concentration of 56 g/l after 116 hours.

Example 2: Production of 2'-FL by a Sucrose Utilizing *E. coli*

Bacterial Strain:

The strain was constructed from *Escherichia coli* K12 strain DH1 which was obtained from the Deutsche Sammlung von Mikroorganismen (reference DSM 5346) by deleting the genes: lacZ nanKETA lacA melA wcaJ mdoH and by inserting a Plac promoter to upstream the gmd gene. In addition the starin contains the two following plasmids:

pBS-futC-scrBR-amp which is a pUC derivative carrying the futC gene encoding an α-1,2-fucosyl transferase, the scrR gene encoding a sucrose repressor, the scrB gene encoding a sucrose-6-phosphate hydrolase and the ampicillin resistance gene;

pBBR3-GMAB-scrYA-tet which is a pBBR1-MCS3 derivative carrying the manB, manC, gmd and wcaG genes involved in the GDP-Fuc biosynthesis, the scrA gene encoding a PTS system sucrose-specific EIIBC component, the scrYgene encoding a sucrose porin and the tetracycline resistance gene.

Fermentation Procedure:

Sucrose and lactose were each sterilized at 120° C. Isopropyl thio-β-D-galactopyranoside (IPTG) was filter sterilized.

The culture was carried out in a 2 l fermenter containing ≈0.9 l of mineral culture medium (Samain et al. *J. Biotechnol.* 72, 33 (1999); does not contain antibiotics). The temperature was kept at 33° C. and the pH regulated at 6.8 with 28% NH₄OH. The inoculum of the producing strain consisted in a M9 medium supplemented with sucrose (20 ml) was added to the fermenter. The exponential growth phase started with the inoculation and stopped until exhaustion of sucrose (≈22 g/l) initially added to the medium. The inducer (isopropyl thio-β-D-galactopyranoside, IPTG, 1-2 ml of a 50 mg/ml solution) was then added. A feeding with a lactose+sucrose solution (160 g of lactose+500 g of sucrose/l in water) started with a rate of 9 ml/h for 6 hours, then was continued for 115 hours at a rate of 6 ml/h. The concentration of 2'-FL was around 100 g/l in the supernatant at the end of the fermentation.

The invention claimed is:

1. A genetically modified microorganism capable of making a recombinant oligosaccharide, comprising:
    a recombinant gene encoding a glycosyl transferase which can transfer a glycosyl residue of an activated sugar nucleotide to a carbohydrate acceptor internalized by the microorganism,
    a biosynthetic pathway for making said activated sugar nucleotide from sucrose,
    one or more genes encoding a heterologous PTS-dependent sucrose utilization system so that said cell is capable to use sucrose as a carbon source for making said activated sugar nucleotide and as an energy source, and
    wherein said genetically modified microorganism is an $E.$ $coli$ cell of LacZ$^-$ genotype and comprises a galactosyl transferase capable of transferring a galactosyl residue of UDP-Gal to lacto-N-triose,
    said recombinant oligosaccharide is lacto-N-neotetraose (LNnT),
    said carbohydrate acceptor is lactose,
    said activated sugar nucleotide is UDP-GlcNAc,
    said glycosyl transferase is an N-acetyl-glucosaminyl transferase,
    said glycosyl residue is GlcNAc,
    said heterologous PTS-dependent sucrose utilization system comprises proteins encoded by scr genes scrY, scrA, scrB and scrR.

2. The genetically modified microorganism of claim 1, wherein said scr genes are on two plasmids in said cell with one plasmid carrying scrA and another plasmid carrying scrB.

3. The genetically modified microorganism of claim 1, wherein the genetically modified microorganism further comprises a deleted lacA gene.

4. The genetically modified microorganism of claim 3, wherein the genetically modified microorganism further comprises a deleted lacI gene.

5. A process for making a recombinant lacto-N-neotetraose (LNnT), comprising the steps of:
    a) providing the genetically modified microorganism of claim 1
    b) culturing said genetically modified microorganism in the presence of lactose and sucrose, and
    c) separating lacto-N-neotetraose (LNnT) from said genetically modified microorganism, from the culture medium, or from both.

6. The process according to claim 5, wherein said cell comprises a deleted lacA gene.

7. The process according to claim 6, wherein said cell comprises a deleted lacI gene.

8. The process according to claim 5, wherein the culturing step comprises:
    culturing said cell in a fermentation broth containing lactose and sucrose, thereby inducing
        internalization of said lactose into said cell via an active transport mechanism, and
        formation of said lacto-N-neotetraose (LNnT), and
    utilizing sucrose as a carbon source for biosynthesis of UDP-GlcNAc in said genetically modified microorganism.

* * * * *